US006976758B2

(12) United States Patent
Khaw et al.

(10) Patent No.: US 6,976,758 B2
(45) Date of Patent: Dec. 20, 2005

(54) GONIOSCOPY LENS

(75) Inventors: Peng Tee Khaw, London (GB); Peter G. Harrington, Seattle, WA (US); Daniel M. Bell, Renton, WA (US)

(73) Assignee: Ocular Instruments, Inc., Bellevue, WA (US)

( * ) Notice: Subject to any disclaimer, the term of this patent is extended or adjusted under 35 U.S.C. 154(b) by 454 days.

(21) Appl. No.: 10/408,674

(22) Filed: Apr. 4, 2003

(65) Prior Publication Data

US 2004/0196434 A1 Oct. 7, 2004

(51) Int. Cl.[7] ............................ A61B 3/00; A61B 3/10

(52) U.S. Cl. ...................................... 351/219; 351/205

(58) Field of Search ........................................ 351/219

(56) References Cited

U.S. PATENT DOCUMENTS 3,820,879 A 6/1974 Frisen
4,033,679 A 7/1977 Sussman
4,410,245 A * 10/1983 Koester ...................... 351/219
4,439,026 A 3/1984 Wilms
4,506,962 A * 3/1985 Roussel ...................... 351/219
4,598,984 A * 7/1986 Rol ........................... 351/219
5,252,998 A 10/1993 Reis et al.
5,479,222 A * 12/1995 Volk .......................... 351/219
5,501,217 A 3/1996 Ishiguro et al.
6,698,886 B2 * 3/2004 Pollack et al. .............. 351/219

OTHER PUBLICATIONS

Iwasaki, N., M.D., et al., "The Double-Mirror Gonioscopic Lens for Surgery of the Anterior Chamber Angle," *Arch Ophthalmol 115*:1333-1335, Oct. 1997.
Diagnostic Lenses, "Direct View Gonio Lens," Ocular Instruments, Inc. Catalog, p. 5, 1997.
Special Order Lenses, "Direct View Gonio Lens," Ocular Instruments, Inc. Catalog, p. 18, 1997.
Surgical Lens Sets, "Tano Double Mirror Surgical Gonio," Ocular Instruments, Inc. Catalog, p. 23, 1997.
Diagnostic Lenses, "Ocular Sussman Four Mirror Hand Held Gonioscope," Ocular Instruments, Inc. Catalog, 1987.

* cited by examiner

*Primary Examiner*—Eleni Mantis-Mercader
*Assistant Examiner*—John R. Sanders
(74) *Attorney, Agent, or Firm*—Christensen O'Connor Johnson Kindness PLLC

(57) ABSTRACT

A gonioscopy lens employs a plurality of mirror sets so that substantially the entire periphery of the anterior chamber of an eye can be viewed without rotating or moving the contact lens. Each mirror set comprises a first mirror position anterior to the eye on one side of the optical axis and a second mirror positioned posterior to the first mirror on the opposite side of the optical axis. Each set is oriented relative to each other so that the second mirror receives light rays from the peripheral portion of the anterior chamber, reflects those rays to the second mirror to the first mirror, and then reflects the light rays in a generally anterior direction so that they can be used by an ophthalmologist employing the lens. The image viewed by the ophthalmologist is upright and located over its actual position.

6 Claims, 1 Drawing Sheet

40b 18 16 14 32d 10 32b 34 12 30d 30b 26 42 40 20 22 24

GONIOSCOPY LENS

FIELD OF THE INVENTION

The present invention relates to an ophthalmic diagnosis lens and more particularly to contact lenses for viewing the anterior chamber of an eye.

BACKGROUND OF THE INVENTION

Current gonioscopy lenses are generally of three types. The simplest type comprises a contact lens element having a concave contact lens surface for contacting the cornea of an eye. The lens has a planar mirror (or prism facet) positioned adjacent to and extending anteriorly and laterally outwardly relative to the contact lens surface and the optical axis of the eye. As used herein, mirror or mirror surface is synonymous with prism facet. The mirror is angled such that light rays originating at the periphery of the anterior chamber are reflected outwardly in a direction generally parallel to the optical axis for viewing by the ophthalmologist. More than one mirror may be positioned around the contact lens element so that multiple portions of the eye can be viewed without rotating the lens. Because the image is viewed only through a single mirror, the image viewed by the physician is necessarily inverted. Moreover, it is offset 180° from the actual location of the image being viewed. Because the image is inverted, the lens must be rotated in a direction opposite to the direction one would intuitively move the lens in order to view an adjacent portion of the periphery of the anterior chamber.

A second type of lens commonly called a direct view gonioscopy lens employs a pair of mirror surfaces, one of which is offset from the central axis of the contact lens and the other of which intersects the central axis of the lens. The offset surface originates adjacent a peripheral portion of the contact lens surface and extends anteriorly and laterally therefrom. The second surface extends from a location adjacent and anterior to the bottom portion of the second surface and extends anteriorly from a position on the same side of the central axis as the second surface and intersects the central axis. With this arrangement, the peripheral portion of the anterior chamber can be viewed along the central axis of the lens. With this arrangement, however, only one segment of the periphery of the anterior chamber can be viewed without rotating the lens relative to the eye.

A third type of gonioscopy lens has a first mirror surface on one side of the central axis and a second mirror on the opposite side of the central axis. The two mirror surfaces are juxtaposed on opposite sides of the central axis and are arranged so that light rays from the periphery of the anterior chamber are reflected by the first mirror to the second mirror and then by the second mirror in an anterior direction generally parallel to the central axis. Because the first mirror is positioned on an opposite side of the central axis, the image appears generally to be located above the portion of the anterior chamber being viewed. This mirror arrangement again allows only one portion of the periphery of the anterior chamber to be viewed without rotating the contact lens element.

SUMMARY OF THE INVENTION

The present invention provides a gonioscopy lens that eliminates the disadvantages of the foregoing lenses while also allowing the entire periphery of the anterior chamber to be viewed without rotating the lens. In addition, the upright image being viewed appears to be residing directly over the portion of the anterior chamber actually being viewed.

The lens of the present invention has an central axis alignable with the optical axis of the eye. The lens includes a contact lens element having a concave surface, with a curvature compatible with the cornea of an eye, and a plurality of mirror sets. Each mirror set has a first mirror positioned anterior to the eye and anterior to the region of the anterior chamber to be viewed. A second mirror in each set is positioned posterior to the first mirror on the opposite side of the optical axis of the eye from the first mirror. Each of the mirror sets receives light rays from a peripheral portion of the anterior chamber, reflects those rays from the second mirror to the first mirror, and then reflects the light rays in an anterior direction relative to the eye. The viewed light rays reside in a location generally corresponding to the location of the portion of the periphery of the eye actually being viewed. Because two mirror surfaces are used, an upright image is viewed by the ophthalmologist. In addition, because a multiplicity of mirror surfaces are employed, the entire periphery of the anterior chamber can be viewed without rotating the lens. In a preferred embodiment, the second mirror of each mirror set is positioned wholly posterior to the first mirror of each set.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
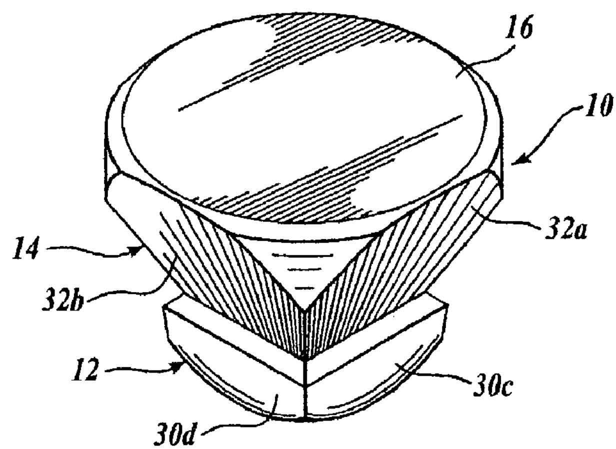
FIG. 1 is an isometric view of the contact lens of the present invention.
Figure 2:
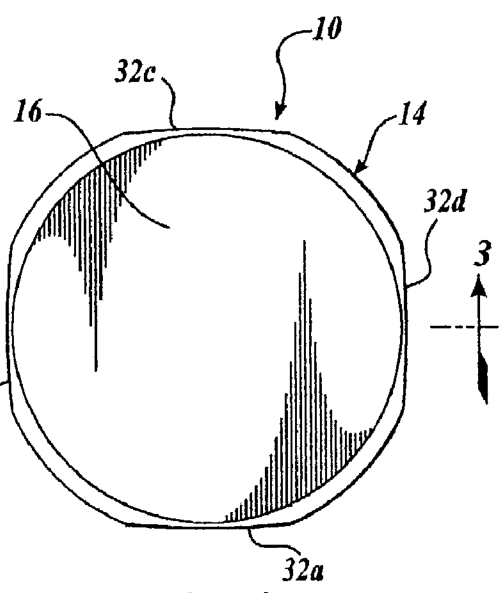
FIG. 2 is a plan view of the lens of the present invention.
Figure 3:
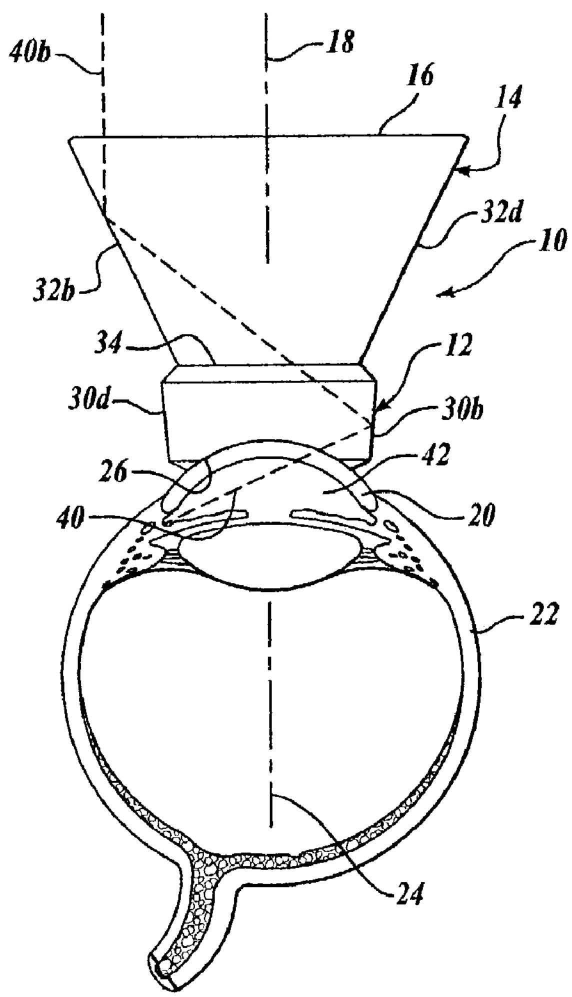
FIG. 3 is a cross-sectional view of the lens of FIG. 2 showing the position on the eye of a patient.
Figure 4:
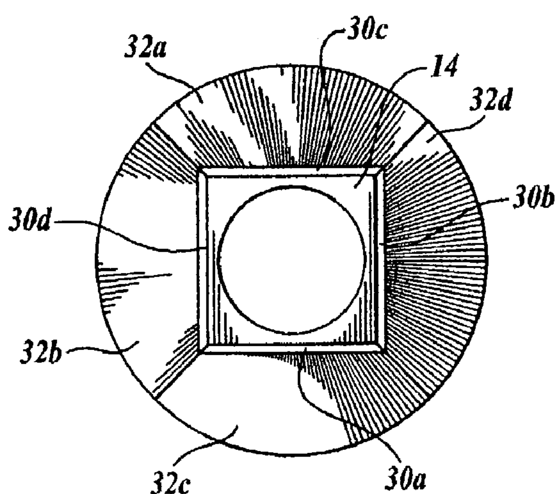
FIG. 4 is a bottom view of the lens of the present invention.

Referring first to FIG. 1, the contact lens 10 of the present invention comprises a lower prism element 12 and an upper prism element 14. In the currently preferred embodiment, both prism elements 12 and 14 are manufactured separately, however, could be machined from a single block of optical material if desired.

Referring now to all the figures, contact lens 10 has an anterior surface 16 that is oriented generally perpendicular to the central axis 18 of the contact lens. The contact lens 10 is shown positioned on the cornea 20 of an eye 22 of a human patient. The central axis 18 of the contact lens 10 is generally aligned with the optical axis 24 of the eye. The posterior prism element 12 has a concave contact lens surface 26 formed in the posterior portion thereof. This concave contact lens surface 26 has a curvature that is designed in a conventional manner to conform to the curvature of an average cornea 20 of the human eye 22. The lower prism 12 has four facets 30*a*, 30*b*, 30*c*, and 30*d*, each positioned laterally outwardly from the central axis of the contact lens 10. In the preferred embodiment, the four facets 30*a*–30*d* are equidistantly spaced about the central axis 18. Each of the facets 30*a*–30*d* is internally reflective. The four facets are generally upright, but are angled laterally outwardly from the posterior edge to the anterior edge.

The anterior surface 16 of the upper element 14 is preferably planar and oriented perpendicularly to the central axis 18. The surface 16, however, may be curved (spheric or aspheric) and may carry a magnifying element as well.

The anterior prism element 14 also has four facets 32*a*, 32*b*, 32*c* and 32*d* that are preferably positioned anterior to the facets 30*a*, 30*b*, 30*c* and 30*d*. In the preferred embodiment, the anterior surface of the posterior prism element 12 is oriented perpendicularly to the central axis 18, while the posterior surface of the anterior element 14 is also oriented perpendicularly to the central axis 18. These two surfaces are joined along a plane 34 with a conventional optical coupling agent and/or cement. The anterior surfaces of the upper prism facets 32*a*–32*d* are also internally reflective. The upper prism facets are also angled laterally outwardly from posterior edge to anterior edge.

Each of the lower facets 30*a*, 30*b*, 30*c* and 30*d* are mated with corresponding upper facets 32*a*, 32*b*, 32*c*, and 32*d*, respectively. Each mated facet, for example 30*b*, is positioned on opposite side of the central axis 18 from the other mated facet, for example 32*b*. The lower facets 30*a*–30*d* are oriented so that, for example, a light ray 40 originating at the periphery of the anterior chamber 42 of the eye travels across the optical axis 24 of the eye 22 and central axis 18 of the contact lens 10 through the cornea 20, and is reflected from the inwardly facing facet 30*b* in the posterior prism element 12. The light ray is then reflected anteriorly and laterally so that it again crosses over the region of the central axis 18 of the lens and intersects the inwardly facing facet 32*b* in the anterior prism element 14. The facet 32*b* is angled such that the light ray is then reflected in an anterior direction generally parallel to the central axis 18 so that it can be viewed by an ophthalmologist employing the lens. The anterior portion 40*b* of the light ray 40 is positioned on the same side of the central axis 18 as the peripheral portion of the anterior chamber 42 being viewed by the ophthalmologist.

In the preferred embodiment, four sets of mated surfaces are employed. This allows virtually 360° coverage of the periphery of the anterior chamber 42 without moving or rotating the lens 10. Fewer than four or more than four sets of facets, for example 8 sets, may be employed. However, it has been found that four is optimum for most purposes.

In the preferred embodiment, the posterior facets 30*a*–30*b* and the contact lens surface 26 are formed in a single optical element, anterior prism 12. The four facets 32*a*–32*d* are also formed in a single prism, posterior element 14. If desired, both prisms 12 and 14 may be integrated into a single optical element. The preferred material from which the prism elements are made is polymethylmethacrylate but other materials such as optical glass, or combinations thereof, may be employed if desired. It is also preferred that the outer surface of the facets 30*a*–30*d* and 32*a*–32*d* be coated with a reflective coating; however, if the entire lens 10 is housed in an opaque housing, it would not be necessary to coat the outer surfaces of the anterior facets 32*a*–32*d*. Also in a preferred embodiment of the invention the facets 32*a*–32*d* are orientated at an angle of about 26 degrees from the central axis 18. Similarly, the facets 30*a*–30*d* are angled about 6 degrees from the central axis 18.

If desired, the entire device may be fixed in a housing in a conventional manner, or may be fitted with a holding ring or a laterally extending handle. The lower element may also be fitted with a conventional contact flange.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A lens for viewing the anterior chamber of an eye, said lens having a central axis alignable with the optical axis of said eye, comprising:

a plurality of mirror sets, each mirror set having a first mirror positioned anterior to the eye and anterior to the region of the anterior chamber to be viewed, and a second mirror positioned posterior to said first mirror and positioned on the opposite side of the optical axis of said eye from said first mirror; and a contact lens having a concave surface with a curvature compatible with the cornea of an eye, said contact lens transmitting light rays to each of said mirror sets from the peripheral portion of the anterior chamber, the rays being reflected from said second mirror to said first mirror, and then being reflected in an anterior direction from said first mirror.

2. The lens of claim 1, wherein said mirror sets are arranged uniformly about said axis so as to make the peripheral portion of the anterior chamber viewable without rotating the lens.

3. The lens of claim 2, comprising four of said mirror sets.

4. The lens of claim 2, wherein said second mirror of each set is positioned wholly in a posterior direction from said first mirror of each set.

5. The lens of claim 2, wherein the posterior edge of said second mirror is positioned posterior to the most anterior portion of said contact lens.

6. The lens of claim 2, wherein said first mirrors are formed in a first solid prism, and said second mirrors and said contact lens are formed in a second solid prism posterior to said first prism, said first and second prisms being optically joined to transmit light rays.

* * * * *